(12) United States Patent
Wu

(10) Patent No.: US 11,166,988 B2
(45) Date of Patent: Nov. 9, 2021

(54) **METHOD OF AMELIORATING CHRONIC OBSTRUCTIVE PULMONARY DISEASE USING *PARABACTEROIDES GOLDSTEINII***

(71) Applicant: Multistars Biotechnology Company Limited, Taoyuan (TW)

(72) Inventor: Po-I Wu, Taoyuan (TW)

(73) Assignee: MULTISTARS BIOTECHNOLOGY COMPANY LIMITED, Taoyuan (TW)

( * ) Notice: Subject to any disclaimer, the term of this patent is extended or adjusted under 35 U.S.C. 154(b) by 0 days.

(21) Appl. No.: 16/541,308

(22) Filed: Aug. 15, 2019

(65) Prior Publication Data

US 2020/0069743 A1 Mar. 5, 2020

Related U.S. Application Data

(60) Provisional application No. 62/726,592, filed on Sep. 4, 2018.

(30) Foreign Application Priority Data

Jan. 25, 2019 (TW) ................................ 108102979

(51) Int. Cl.
*A61K 35/74* (2015.01)
*A61P 11/00* (2006.01)

(52) U.S. Cl.
CPC .............. *A61K 35/74* (2013.01); *A61P 11/00* (2018.01)

(58) Field of Classification Search
None
See application file for complete search history.

(56) References Cited

FOREIGN PATENT DOCUMENTS

WO    WO-2016203220 A1 * 12/2016    ............... C12R 1/01

* cited by examiner

*Primary Examiner* — Brian Gangle
(74) *Attorney, Agent, or Firm* — WPAT, PC

(57) ABSTRACT

The present invention provides a method of improving the weight loss, the emphysema, the infiltration of inflammatory cells in lung tissues, the thickening of the tracheal wall, the lung fibrosis, and the abnormal lung function, which are caused by a chronic obstructive pulmonary disease, comprising administering to a subject in need thereof a therapeutically effective amount of a probiotic bacterium *Parabacteroides goldsteinii*. The bacterium *Parabacteroides goldsteinii* can also modulate the expression level of genes involved in the lung fibrosis and the mitochondrial activity in lung tissue. The bacterium *Parabacteroides goldsteinii* can therefore be used to treat chronic obstructive pulmonary disease.

11 Claims, 10 Drawing Sheets

Specification includes a Sequence Listing.

SEQUENCE LISTING

<160> NUMBER OF SEQ ID NOS: 24

<210> SEQ ID NO 1
<211> LENGTH: 20
<212> TYPE: DNA
<213> ORGANISM: Artificial sequence
<220> FEATURE:

<223> OTHER INFORMATION: PCR primer

<400> SEQUENCE: 1 cgcggttctatttttgttggt                                                    20

<210> SEQ ID NO 2
<211> LENGTH: 20
<212> TYPE: DNA
<213> ORGANISM: Artificial sequence
<220> FEATURE:
<223> OTHER INFORMATION: PCR primer

<400> SEQUENCE: 2 agtcggcatcgtttatggtc                                                     20

<210> SEQ ID NO 3
<211> LENGTH: 20
<212> TYPE: DNA
<213> ORGANISM: Artificial sequence
<220> FEATURE:
<223> OTHER INFORMATION: PCR primer

<400> SEQUENCE: 3 accgcggtcatacgattaac                                                     20

<210> SEQ ID NO 4
<211> LENGTH: 20
<212> TYPE: DNA
<213> ORGANISM: Artificial sequence
<220> FEATURE:
<223> OTHER INFORMATION: PCR primer

<400> SEQUENCE: 4 cccagtttgggtcttagctg                                                     20

<210> SEQ ID NO 5
<211> LENGTH: 22
<212> TYPE: DNA
<213> ORGANISM: Artificial sequence
<220> FEATURE:
<223> OTHER INFORMATION: PCR primer

<400> SEQUENCE: 5 ccgcaagggaaagatgaaag ac                                                  22

<210> SEQ ID NO 6
<211> LENGTH: 20
<212> TYPE: DNA
<213> ORGANISM: Artificial sequence
<220> FEATURE:
<223> OTHER INFORMATION: PCR primer

<400> SEQUENCE: 6 tcgtttggtttcggggtttc                                                     20

<210> SEQ ID NO 7
<211> LENGTH: 20
<212> TYPE: DNA
<213> ORGANISM: Artificial sequence
<220> FEATURE:
<223> OTHER INFORMATION: PCR primer

<400> SEQUENCE: 7 agcattcggaagcatctttg                                                     20

<210> SEQ ID NO 8

```
<211> LENGTH: 20
<212> TYPE: DNA
<213> ORGANISM: Artificial sequence
<220> FEATURE:
<223> OTHER INFORMATION: PCR primer

<400> SEQUENCE: 8 ttgtgaggactggaatgctg                                                    20

<210> SEQ ID NO 9
<211> LENGTH: 22
<212> TYPE: DNA
<213> ORGANISM: Artificial sequence
<220> FEATURE:
<223> OTHER INFORMATION: PCR primer

<400> SEQUENCE: 9 cacccagatgcaaaactttc ag                                                 22

<210> SEQ ID NO 10
<211> LENGTH: 23
<212> TYPE: DNA
<213> ORGANISM: Artificial sequence
<220> FEATURE:
<223> OTHER INFORMATION: PCR primer

<400> SEQUENCE: 10 ctgctctttatacttgctca cag                                                23

<210> SEQ ID NO 11
<211> LENGTH: 19
<212> TYPE: DNA
<213> ORGANISM: Artificial sequence
<220> FEATURE:
<223> OTHER INFORMATION: PCR primer

<400> SEQUENCE: 11 agcacggagtgacccaaac                                                     19

<210> SEQ ID NO 12
<211> LENGTH: 21
<212> TYPE: DNA
<213> ORGANISM: Artificial sequence
<220> FEATURE:
<223> OTHER INFORMATION: PCR primer

<400> SEQUENCE: 12 tgtacgtggctacatggacc t                                                  21

<210> SEQ ID NO 13
<211> LENGTH: 20
<212> TYPE: DNA
<213> ORGANISM: Artificial sequence
<220> FEATURE:
<223> OTHER INFORMATION: PCR primer

<400> SEQUENCE: 13 attccttcatgtcggacgag                                                    20

<210> SEQ ID NO 14
<211> LENGTH: 20
<212> TYPE: DNA
<213> ORGANISM: Artificial sequence
<220> FEATURE:
<223> OTHER INFORMATION: PCR primer

<400> SEQUENCE: 14 actgagaagcccccctcaaat                                                   20
```

```
<210> SEQ ID NO 15
<211> LENGTH: 23
<212> TYPE: DNA
<213> ORGANISM: Artificial sequence
<220> FEATURE:
<223> OTHER INFORMATION: PCR primer

<400> SEQUENCE: 15 tatggagtgacatagagtgtgct                                            23

<210> SEQ ID NO 16
<211> LENGTH: 22
<212> TYPE: DNA
<213> ORGANISM: Artificial sequence
<220> FEATURE:
<223> OTHER INFORMATION: PCR primer

<400> SEQUENCE: 16 ccacttcaatccacccagaa ag                                            22

<210> SEQ ID NO 17
<211> LENGTH: 20
<212> TYPE: DNA
<213> ORGANISM: Artificial sequence
<220> FEATURE:
<223> OTHER INFORMATION: PCR primer

<400> SEQUENCE: 17 tgccatcatgaagccagaga                                               20

<210> SEQ ID NO 18
<211> LENGTH: 20
<212> TYPE: DNA
<213> ORGANISM: Artificial sequence
<220> FEATURE:
<223> OTHER INFORMATION: PCR primer

<400> SEQUENCE: 18 aacatcgcagtctccaagga                                               20

<210> SEQ ID NO 19
<211> LENGTH: 20
<212> TYPE: DNA
<213> ORGANISM: Artificial sequence
<220> FEATURE:
<223> OTHER INFORMATION: PCR primer

<400> SEQUENCE: 19 tacacctgctcctgtgcttc                                               20

<210> SEQ ID NO 20
<211> LENGTH: 20
<212> TYPE: DNA
<213> ORGANISM: Artificial sequence
<220> FEATURE:
<223> OTHER INFORMATION: PCR primer

<400> SEQUENCE: 20 cattcctcccactccagact                                               20

<210> SEQ ID NO 21
<211> LENGTH: 20
<212> TYPE: DNA
<213> ORGANISM: Artificial sequence
<220> FEATURE:
<223> OTHER INFORMATION: PCR primer
```

```
<400> SEQUENCE: 21 tcgtagcaaaccaccaagtg                                                    20

<210> SEQ ID NO 22
<211> LENGTH: 20
<212> TYPE: DNA
<213> ORGANISM: Artificial sequence
<220> FEATURE:
<223> OTHER INFORMATION: PCR primer

<400> SEQUENCE: 22 ttgtctttgagatccatgcc                                                    20

<210> SEQ ID NO 23
<211> LENGTH: 20
<212> TYPE: DNA
<213> ORGANISM: Artificial sequence
<220> FEATURE:
<223> OTHER INFORMATION: PCR primer

<400> SEQUENCE: 23 gcttccttgtgcaagtgtct                                                    20

<210> SEQ ID NO 24
<211> LENGTH: 20
<212> TYPE: DNA
<213> ORGANISM: Artificial sequence
<220> FEATURE:
<223> OTHER INFORMATION: PCR primer

<400> SEQUENCE: 24 ggtggcatttcacagttgag                                                    20
```

METHOD OF AMELIORATING CHRONIC OBSTRUCTIVE PULMONARY DISEASE USING *PARABACTEROIDES GOLDSTEINII*

CROSS-REFERENCE TO RELATED APPLICATION

This application claims priority of U.S. provisional application No. 62/726,592, filed on Sep. 4, 2018, and priority of Taiwan patent application No. 108102979, filed on Jan. 25, 2019, the content of which are incorporated herein in its entirety by reference.

BACKGROUND OF THE INVENTION

This applicant incorporates by reference the material in the Sequence Listing submitted via ASCII text file titled Sequencelisting, which is identical to the "Sequence Listing" part of the disclosure.

1. Field of the Invention

The present invention relates to a method of using a probiotic bacterium *Parabacteroides goldsteinii*, and more particularly to a method of using the probiotic bacterium *Parabacteroides goldsteinii* for ameliorating chronic obstructive pulmonary disease, comprising the amelioration of the abnormal lung function, the infiltration of inflammatory cells in lung tissues, the thickening of the tracheal wall, the emphysema, the lung fibrosis, and the mitochondrial activity, which are caused by chronic obstructive pulmonary disease (COPD).

2. The Prior Art

Chronic obstructive pulmonary disease (COPD) is a composite term that is used for patients with emphysema and chronic bronchitis. At the year of 2020, COPD is expected to rank as the third highest disease causing human mortality worldwide and is impressively associated with chronic cigarette smoke (CS) exposure. The tissues from patients with COPD are characterized by chronic inflammation, mucus metaplasia, alveolar destruction, and structural cell apoptosis. Besides, patients with COPD often have the problem of weight loss, which mainly due to increased basic energy consumption reduced nutrient intake, and poor metabolic efficiency. Malnutrition in patients with COPD would cause respiratory muscle weakness, and further cause complications such as hypoxia or carbon dioxide retention. In addition, malnutrition would also cause a decline in immune function and increase the frequency and severity of lung infections.

Recent studies have also highlighted the interesting observation that the airways in COPD tissues are often remodeled and fibrotic while the nearby alveoli manifest tissue rarefication and septal rupture. The inflammation in COPD tissues is felt to be causally related to the emphysema and other pathologic alterations in the lungs from these patients and worsens with disease progression. The mechanisms that mediate these inflammatory and remodeling responses, however, are not adequately understood. A significant amount of the morbidity and mortality in COPD is due to acute exacerbations characterized by cough, shortness of breath, sputum production, and decreases in expiratory airflow. The frequency of these exacerbations correlates with the rate of disease progression and loss of lung function as well as the overall health status of the patient. Thus, exacerbations are now considered to be legitimate targets for disease therapy. However, the mechanisms that mediate these exacerbations and their effects on tissue inflammation and remodeling have not been adequately defined.

Recent researches had showed that airway microbiota was associated with persistent chronic airway inflammation in COPD patients and also played an important role in COPD severity and contributed COPD exacerbation. Moreover, prior studies also showed that the dynamic airway microbiota-dysbiosis and the changes of microbial composition could potentially affect disease development and the progression in COPD. The currently study showed that the faecal microbiota is characterized by an increase in the abundance of *Bacteroides-Prevotella* in 'healthy' smokers, and a decreased Firmicutes/Bacteroidetes ratio compared with non-smokers. Smokers also have a decreased abundance of *Bifidobacterium* spp. and hence may lose the anti-inflammatory effects that are often associated with this genus. However, no study to date has investigated changes in the gut microbiota of patients with COPD. In the present invention, we utilize a composition of the *Parabacteroides goldsteinii* (*P. goldsteinii*) strains to treat chronic obstructive pulmonary disease and provide as a new treatment for new generation probiotics for repairing mitochondrial dysfunction caused by diseases.

SUMMARY OF THE INVENTION

An objective of the present invention is to provide a method of using a probiotic bacterium *Parabacteroides goldsteinii*, the metabolite thereof, or the bacterial component thereof for modulating the physiology of a subject in need thereof to inhibit or treat a chronic obstructive pulmonary disease (COPD).

To solve the foregoing problem, the present invention provides a method of preventing or treating a chronic obstructive pulmonary disease (COPD), comprising administering to a subject in need thereof a composition comprising an effective amount of *Parabacteroides goldsteinii* (*P. goldsteinii*), a metabolite thereof, or the bacterial component thereof, wherein the *P. goldsteinii* is DSM32939. The subject with COPD is administered the composition to ameliorate the weight loss, the infiltration of inflammatory cells in lung tissues, pro-inflammatory cytokine accumulation, airway smooth muscle hyperplasia, the emphysema, the lung fibrosis, or mitochondrial dysfunction, which are caused by COPD, to prevent or treat the COPD. The *P. goldsteinii* reduces the gene expression level of IL-1β, TNF-α, COL3A1, or PGC-1α to reduce the inflammation in lung cells, the lung fibrosis or oxidative stress in lung cells; simultaneously, the *P. goldsteinii* enhances the gene expression level of Cytb, NRF-1, RNR-1, RNR-2, SIRT1, or TFAM to enhance the mitochondrial activity of lung cells.

According to an embodiment of the present invention, the *P. goldsteinii* is a live bacterium; and the composition further comprises bacteria other than *P. goldsteinii*.

According to an embodiment of the present invention, the effective amount of the *P. goldsteinii* is at least $5 \times 10^9$ CFUs/kg of body weight per day, and the administration period may be around 12 weeks.

The use of the *P. goldsteinii* of the present invention in the prevention or treatment of COPD can be, but is not limited to, oral administration to the subject in need thereof. The composition can be orally administered along with food; therefore, the preparation of the composition comprising the *P. goldsteinii* can further include a protein, a monosaccharide, a disaccharide, an oligosaccharide, an oligosaccharide, a polysaccharide, a carbohydrate, an amino acid, a lipid, a vitamin, or any combination well-known in the art.

Otherwise, the preparation of the composition comprising the *P. goldsteinii* can further include a pharmaceutically acceptable excipient, carrier, adjuvant, or food additive. The composition is in the form of a spray, a solution, a semi-solid state, a solid state, a gelatin capsule, a soft capsule, a tablet, ab oral strip, a chewing gum or a freeze-dried powder preparation. Simultaneously, the *P. goldsteinii* or the composition containing can further use in the preparation of a food, a health food, dietary supplement or vaccine composition.

In the method of preventing or treating the COPD, comprising administering to the subject in need thereof the composition comprising the effective amount of the *P. goldsteinii*, wherein the *P. goldsteinii* can improve the weight loss, the emphysema, the infiltration of inflammatory cells in lung tissues, the thickening of the tracheal wall, the lung fibrosis, and the abnormal lung function, which are caused by the COPD, to reduce the inflammatory responses of lung cells such as the accumulation of pro-inflammatory cytokine, the airway smooth muscle hyperplasia, and emphysema, and to alleviate worsening lung function. The *P. goldsteinii* can also reduce the gene expression level of IL-1β, TNF-α, COL3A1, or PGC-1α in lung tissues to reduce the inflammation in lung cells, the lung fibrosis or oxidative stress in lung cells; simultaneously, the *P. goldsteinii* can enhance the gene expression level of Cytb, NRF-1, RNR-1, RNR-2, SIRT1, or TFAM to enhance the mitochondrial activity of lung cells and to repair the mitochondrial dysfunction caused by COPD. Therefore, the use of the characteristics of the *P. goldsteinii* of the present invention provides an innovative strategy for preventing or treating the COPD.

The embodiments of the present invention are further described with the following drawings. The following embodiments are given to illustrate the present invention and are not intended to limit the scope of the present invention, and those having ordinary skill in the art can make some modifications and refinements without departing from the spirit and scope of the present invention. Therefore, the scope of the present invention is defined by the scope of the appended claims.

DETAILED DESCRIPTION OF THE PREFERRED EMBODIMENT

Definition

Figure 1:
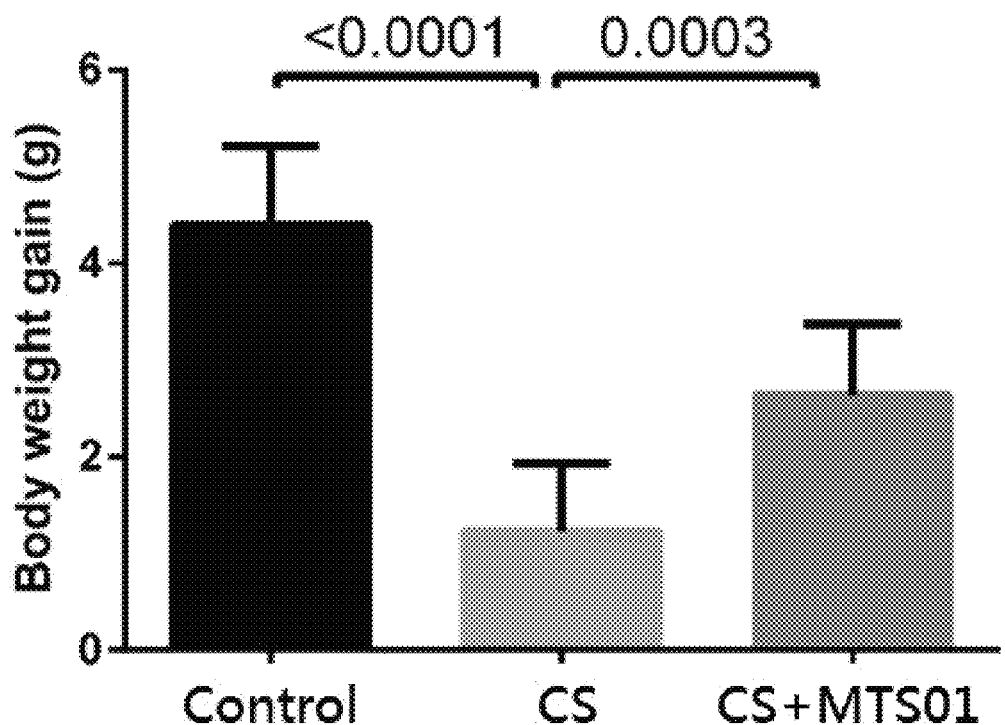
FIG. 1 shows that the *P. goldsteinii* improves the average body weight lost (gram) in the COPD mice model.

The "effective amount" describes herein is the amount of the needed amount of the *P. goldsteinii* that can improve of the weight loss, the emphysema, the infiltration of inflammatory cells in lung tissues, the thickening of the tracheal wall, the lung fibrosis, and the abnormal lung function, which are caused by the COPD in mammals or humans, or can effectively reduce the gene expression level of IL-1β, TNF-α, COL3A1, or PGC-1α in lung tissues and enhance the gene expression level of Cytb, NRF-1, RNR-1, RNR-2, SIRT1, or TFAM in lung tissue. The effective amount varies depending on the species or individual being treated, but the effective amount can be determined experimentally by, for example, a dose escalation test.

The data provides in the present invention represent approximated, experimental values that vary within a range of ±20%, preferably ±10%, and most preferably ±5%.

According to the present invention, the operating procedures and parameter conditions for bacterial culture are within the professional literacy and routine techniques of those having ordinary skill in the art.

The "metabolite" describes herein is a substance which is secreted into the bacterial culture solution after being metabolized by the bacteria.

The "the bacterial component thereof" describes herein is a derivative substance directly or indirectly related to the bacterium when it is cultured, including but not limited to the metabolic product of the bacterium, the structure of the bacterium, the bacteria-related activity and the inactive ingredient, etc.

The "probiotic or probiotic bacteria" describes herein is a microorganism the cells thereof, the mixed strains, the extracts or the metabolites with a positive effect on the host itself, usually derived from the human body and beneficial to intestinal health. Probiotic or probiotic bacteria can also refer to certain microorganisms that are externally supplemented and are beneficial to the body.

The prevent invention provides a method of preventing or treating the COPD, comprising administering to the subject in need thereof the composition comprising an effective amount of the *P. goldsteinii*. The following experiments show that the *P. goldsteinii* of the present invention improves the weight loss, the emphysema, the infiltration of inflammatory cells in lung tissues, the thickening of the tracheal wall, the lung fibrosis, and the abnormal lung function, which are caused by the COPD in mammals or humans, or can effectively reduce the gene expression level of IL-1β, TNF-α, COL3A1, or PGC-1α in lung tissues and enhance the gene expression level of Cytb, NRF-1, RNR-1, RNR-2, SIRT1, or TFAM in lung tissue. In general, the effective amount of a mammal or a human of the *P. goldsteinii* of the present invention is at least $5 \times 10^9$ CFUs/kg of body weight per day, as described in detail below.

The Strain of the *Parabacteroides goldsteinii* of the Present Invention

*Parabacteroides goldsteinii* (*P. goldsteinii*) MTS01 used in the examples of the present invention is deposited in Deutsche Sammlung von Mikroorganismen and Zellkulturen (DSMZ), German on Oct. 29, 2018, and the number is DSM 32939. *P. goldsteinii* is an obligate anaerobe that needs to be cultured in an anaerobic incubator at 37° C. for about 48 hours. The liquid culture medium of the *P. goldsteinii* is NIH thioglycollate broth (TGC II) (purchased from BD, USA, No. 225710), and the solid culture medium is Anaerobic blood agar plate (Ana. BAP) (purchased from CREATIVE LIFESCIENCES, Taiwan). The *P. goldsteinii* is stored in a −80° C. refrigerator for a long-term preservation, and the protective liquid is 25% glycerin. It does not need special cooling treatment and can be stored by freeze drying to stabilize its activity. In the examples of the present invention, it is confirmed through the animal experiments that feeding the live strain of the *P. goldsteinii* of the present invention improves the weight loss, the emphysema, the infiltration of inflammatory cells in lung tissues, the thickening of the tracheal wall, the lung fibrosis, and the abnormal lung function, which are caused by the COPD; the *P. goldsteinii* also. reduce the gene expression level of IL-1β, TNF-α, COL3A1, or PGC-1α in lung tissues to reduce the inflammation in lung cells, the lung fibrosis or oxidative stress in lung cells, and simultaneously, the *P. goldsteinii* enhances the gene expression level of Cytb, NRF-1, RNR-1, RNR-2, SIRT1, or TFAM to enhance the mitochondrial activity of lung cells and to repair the mitochondrial dysfunction caused by COPD. These results demonstrate that the *P. goldsteinii* of the present invention can be used for the preparation of a pharmaceutical composition for preventing or treating COPD.

According to the present invention, the operating procedures and parameter conditions for bacterial culture are within the professional literacy and routine techniques of those having ordinary skill in the art.

Experimental Mice

In the present invention, eight-week to 10-week-old, specific pathogen-free, C57BL/6 female mice were purchased from the Jackson Laboratory (Bar Harbor, USA). All mice were fed ad libitum with chow and water. Animals were housed in a specific pathogen-free facility and were treated in accordance with guidelines from the National Institutes of Health (USA).

The animal groups consist of (1) Mice exposed to room air for twelve weeks and fed with PBS oral gavage once per day (control group); (2) Mice exposed to smoke from twelve 3R4F cigarettes (Kentucky University, USA) twice a day (a total of twenty-four cigarettes per day) for twelve weeks to be induced with COPD and fed with PBS oral gavage once per day (CS group); (3) Mice exposed to smoke in the same method as the CS group to be induced with COPD and fed with $1 \times 10^8$ *P. goldsteinii* orally gavage once per day (CS+MTS01 group), and n=10 for each of these three groups.

Example 1

Effect of *Parabacteroides goldsteinii* on Body Weight in Chronic Obstruction Pulmonary Mice In order to investigate the effect of *P. goldsteinii* on improving the weight loss caused by the COPD, each of these three mouse model groups were monitored the body weight every week during the 12 weeks of the experimental duration. The calculation formula of body weight gain is final body weight (12 week) minus body weight of start point (0 week). For body weight change, the value of body weight gain divides to original body. The value presented by gram (FIG. 1) or percentage (FIG. 2). All statistical analyses were performed using standard one-way ANOVA with Dunnett's multiple comparison test (GraphPad prism 4.01; GraphPad Software Inc., San Diego, Calif.) (* $p<0.05$;  $p<0.01$; * $p<0.001$).

Figure 2:
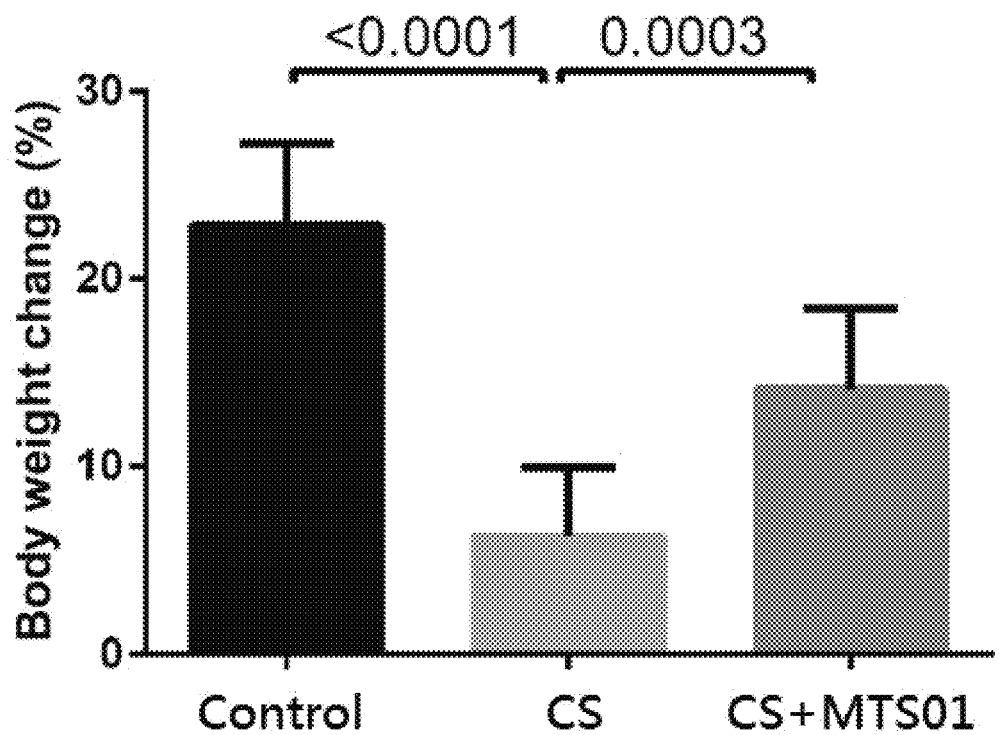
FIG. 2 shows that the *P. goldsteinii* improves the average body weight lost (percentage) in the COPD mice model.

The results of the *P. goldsteinii* of the present invention for improving the weight loss of CS-induced COPD mice are shown in FIG. 1 and FIG. 2. As showing in FIG. 1 and FIG. 2, compared with the control group, the body weight gain of the mice in the CS group significantly reduced after being induced with COPD by CS. However, compared with the CS group, the body weight gain of the mice in the CS+MST01 group significantly increased after being induced with COPD by CS and simultaneously fed the *P. goldsteinii* of the present invention. The results demonstrate that the *P. goldsteinii* of the present invention can effectively improve the problem of the weight loss of individuals caused by COPD.

Example 2

Effect of *Parabacteroides goldsteinii* on the Emphysema, the Thickening of the Tracheal Wall, and the Lung Fibrosis in Chronic Obstruction Pulmonary Mice In order to investigate the effect of *P. goldsteinii* on improving the emphysema, the thickening of the tracheal wall, the lung fibrosis caused by the COPD, the lungs of each of these three mouse model groups were fixed in buffered formalin and embedded in paraffin. Thin sections (4 mm) were prepared and stained with hematoxylin and eosin (H&E). Stained sections were examined under an optical light microscope (Olympus, Tokyo, Japan). Histological images were analyzed using the ImageJ software (National Institutes of Health, Bethesda, USA). Two randomly-selected fields from each 10-15 sections were analyzed.

Figure 3:
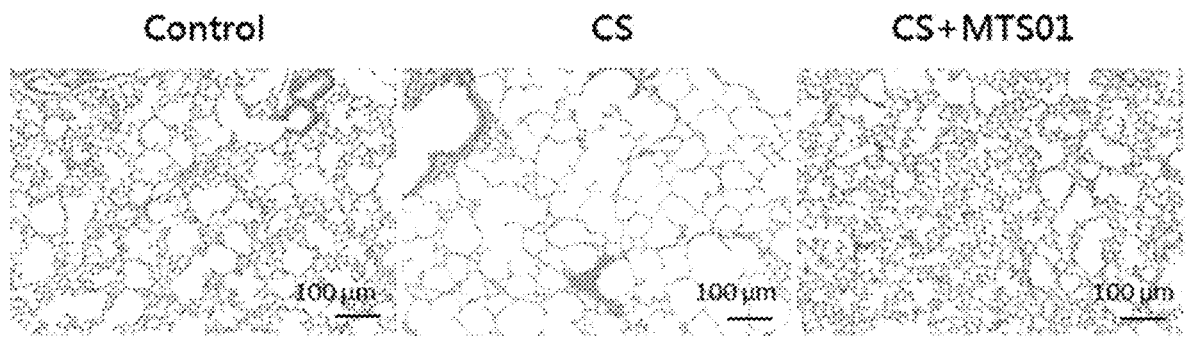
FIG. 3 shows that the *P. goldsteinii* improves the emphysema in the lung tissue in the COPD mice model.

The results of the *P. goldsteinii* of the present invention for improving the emphysema of CS-induced COPD mice are shown in FIG. 3. As showing in FIG. 3, compared with the control group, the alveolar wall of the mice in the CS group became thinner and was damaged more seriously. However, compared with the CS group, the emphysema of the mice in the CS+MST01 group significantly improved after being induced with COPD by CS and simultaneously fed the P. goldsteinii of the present invention. The results demonstrate that the P. goldsteinii of the present invention can effectively improve the problem of the emphysema of individuals caused by COPD.

Figure 4:
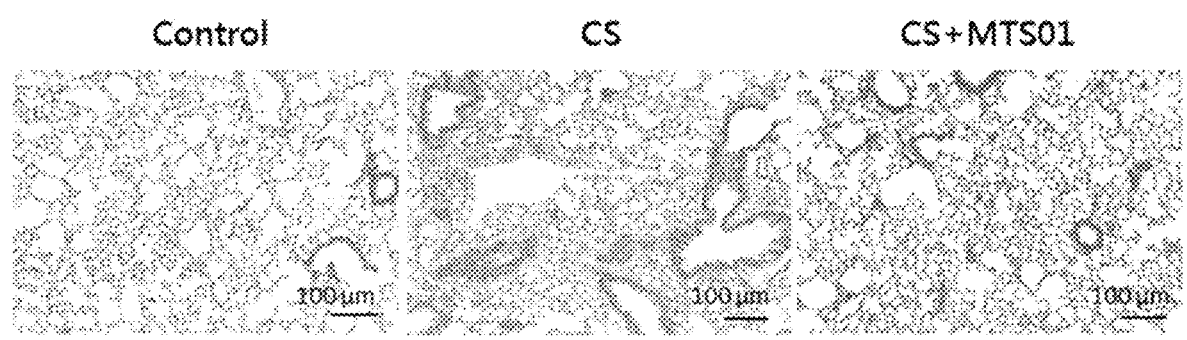
FIG. 4 shows that the *P. goldsteinii* improves the infiltration of inflammatory cells in lung tissues, the thickening of the tracheal wall, and the lung fibrosis in the lung tissue in the COPD mice model.

The results of the P. goldsteinii of the present invention for improving the thickening of the tracheal wall and the lung fibrosis of CS-induced COPD mice are shown in FIG. 4. As showing in FIG. 4, compared with the control group, in the lung tissues, the thickening of the tracheal wall and the lung fibrosis of the mice in the CS group was more seriously. However, compared with the CS group, the thickening of the tracheal wall and the lung fibrosis of the mice in the CS+MST01 group significantly improved after being induced with COPD by CS and simultaneously fed the P. goldsteinii of the present invention. The results demonstrate that the P. goldsteinii of the present invention can effectively improve the problem of the thickening of the tracheal wall, and the lung fibrosis of individuals caused by COPD.

Example 3

Effect of Parabacteroides goldsteinii on the Abnormal Lung Function in Chronic Obstruction Pulmonary Mice In order to investigate the effect of P. goldsteinii on improving the abnormal lung function caused by the COPD, after whole-body plethysmography, all mice of each of these three mouse model groups were anesthetized, tracheostomized, and placed in a forced pulmonary maneuver system (Buxco Research Systems, Wilmington, N.C.). An average breathing frequency of 100 breaths/min was imposed on the anesthetized animals. Three semi-automatic maneuvers including the Boyle's law functional residual capacity (FRC), quasistatic P-V, and fast flow volume maneuver were performed with the Buxco system. The FRC was determined with Boyle's law FRC.

To measure total lung capacity (TLC), residual volume (RV), inspiratory capacity (IC), vital capacity (VC), expiratory reserve volume (ERV), and chord compliance (Cchord), the quasistatic PV maneuver was performed.

Under the fast flow volume maneuver, forced expiratory flows (FEFs, including peak expiratory flow rate (PEF) and forced expiratory flow rate (FEF)), times of expiration and inspiration (Te, and Ti), and forced expiratory volume (FEVs) such as forced vital capacity (FVC), FEV at 100 ms (FEV100), and FEV at 200 ms (FEV200) were recorded.

All maneuvers and perturbations were performed until three correct measurements were achieved. For each parameter, an average of three measurements was calculated and depicted per mouse. The result values were displayed as mean±standard deviation and all statistical analyses were performed using standard one-way ANOVA with Dunnett's multiple comparison test (GraphPad prism 4.01; GraphPad Software Inc., San Diego, Calif.). With these tests, the pulmonary parameters in different groups are compared with those from control group (* $p<0.05$;  $p<0.01$; * $p<0.001$).

Figure 5:
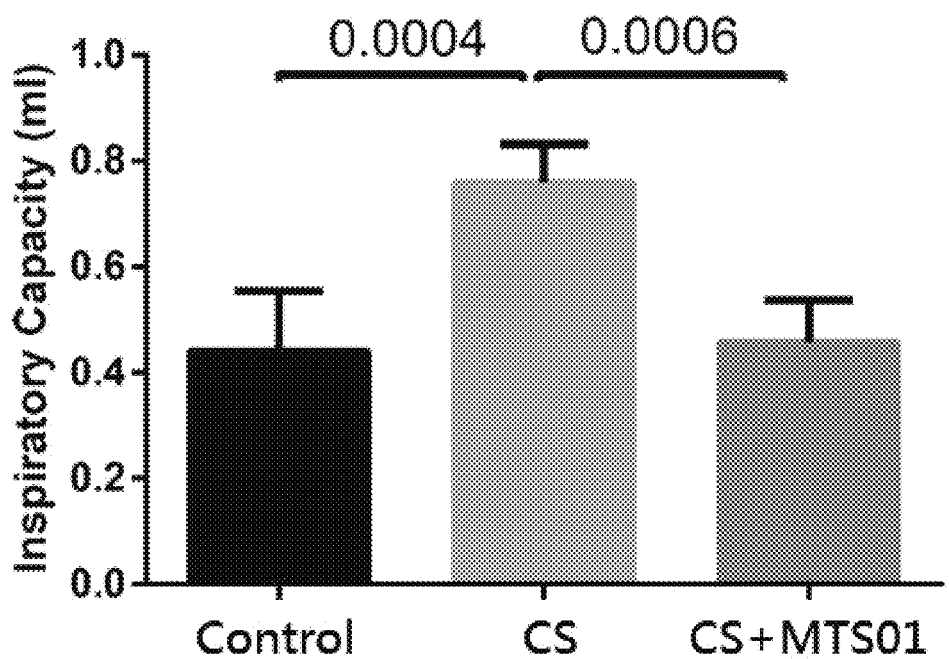
FIG. 5 shows that the *P. goldsteinii* improves the abnormal lung function of inspiratory capacity in the COPD mice model.
Figure 6:
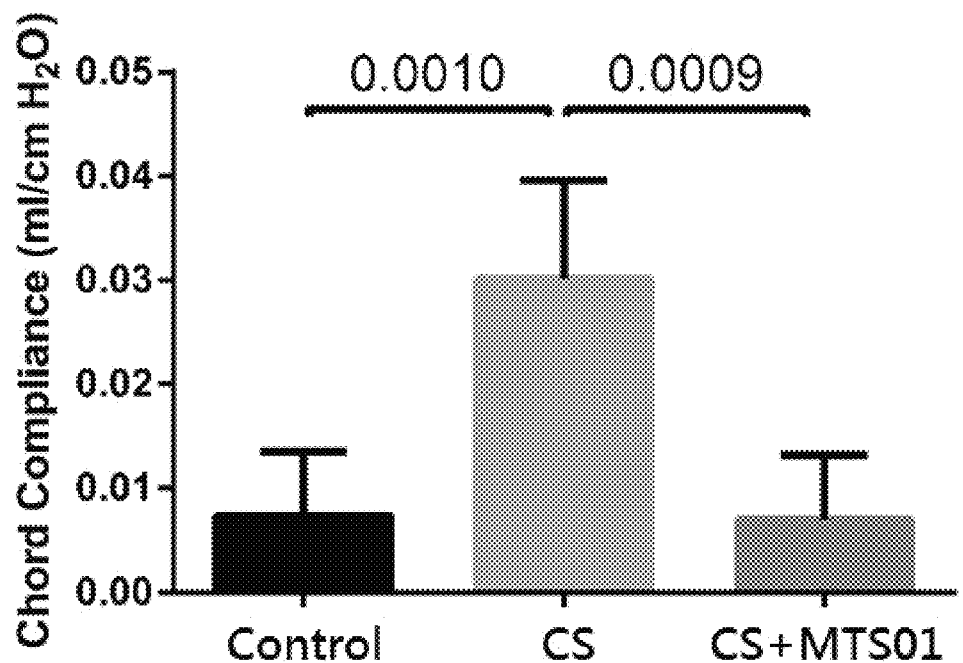
FIG. 6 shows that the *P. goldsteinii* improves the abnormal lung function of lung chord compliance (Cchord) in the COPD mice model.
Figure 7:
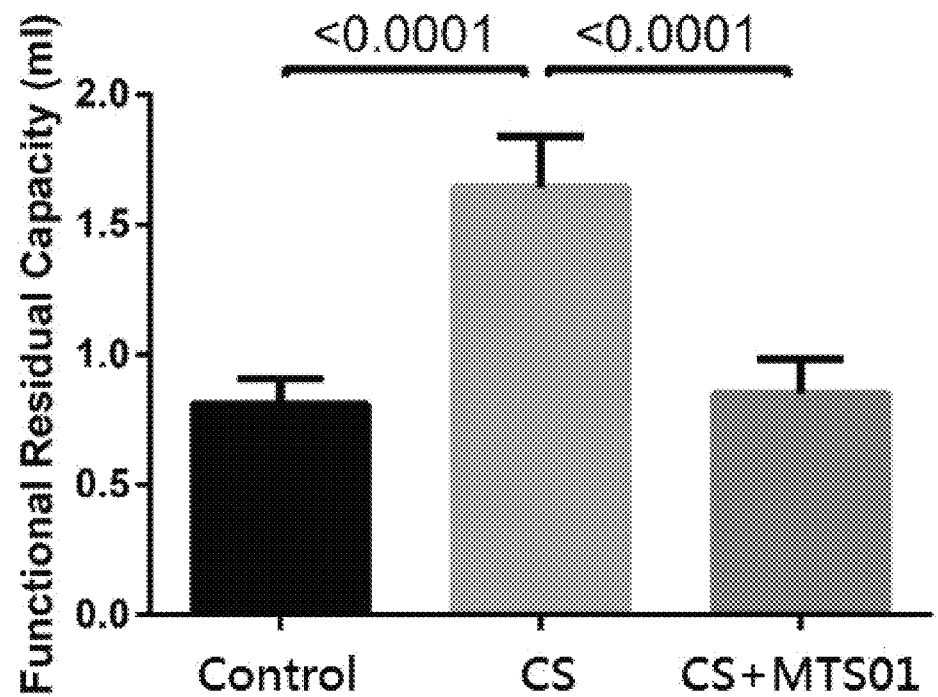
FIG. 7 shows that the *P. goldsteinii* improves the abnormal lung function of functional residual capacity in the COPD mice model.
Figure 8:
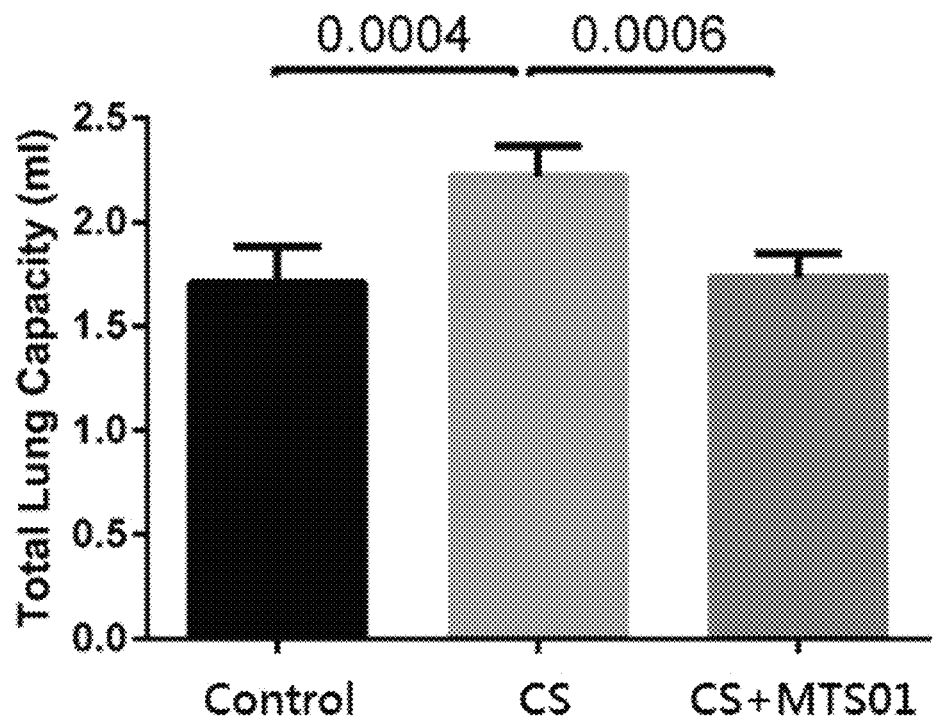
FIG. 8 shows that the *P. goldsteinii* improves the abnormal lung function of total lung capacity in the COPD mice model.
Figure 9:
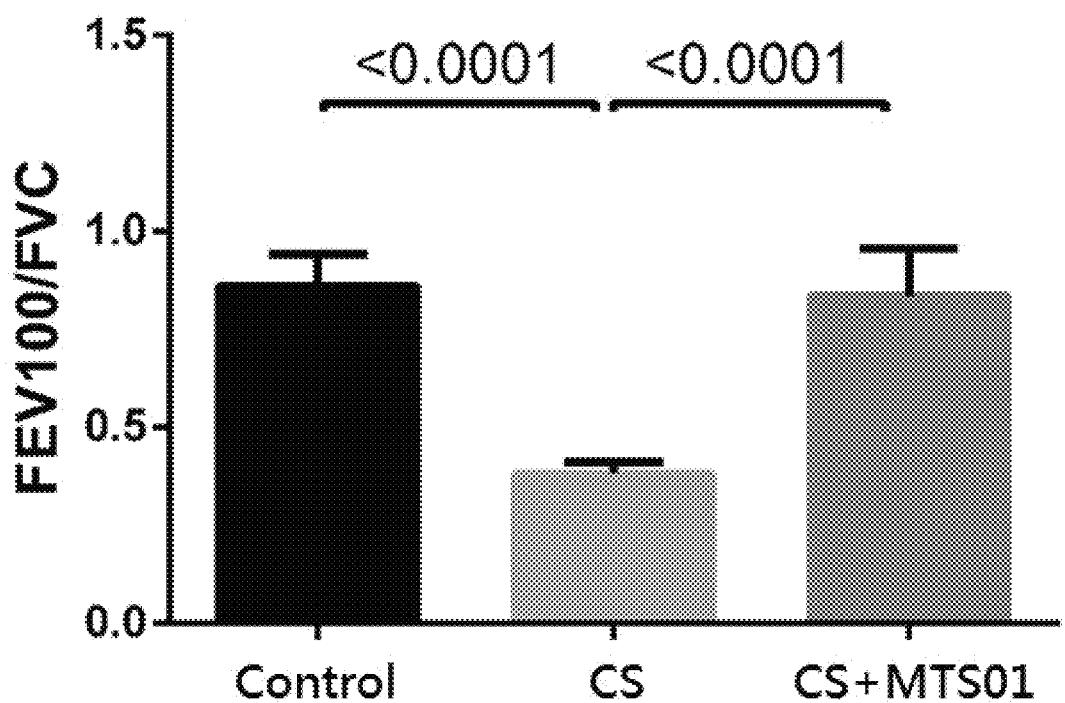
FIG. 9 shows that the *P. goldsteinii* improves the abnormal lung function of forced expiratory volume 100 ms/forced vital capacity in the COPD mice model.

The results of the P. goldsteinii of the present invention for improving the abnormal lung function of inspiratory capacity of CS-induced COPD mice are shown in FIG. 5; the results of the P. goldsteinii of the present invention for improving the abnormal lung function of lung chord compliance (Cchord) of CS-induced COPD mice are shown in FIG. 6; the results of the P. goldsteinii of the present invention for improving the abnormal lung function of functional residual capacity of CS-induced COPD mice are shown in FIG. 7; the results of the P. goldsteinii of the present invention for improving the abnormal lung function of total lung capacity of CS-induced COPD mice are shown in FIG. 8; the results of the P. goldsteinii of the present invention for improving the abnormal lung function of forced expiratory volume 100 ms/forced vital capacity of CS-induced COPD mice are shown in FIG. 9.

As showing in FIG. 5 to FIG. 9, compared with the control group, the lung function of inspiratory capacity, lung chord compliance, functional residual capacity, and total lung capacity of the mice in the CS group significantly increased and the lung function of forced expiratory volume 100 ms/forced vital capacity of the mice in CS group significantly decreased. However, compared with the CS group, the lung function of inspiratory capacity, lung chord compliance, functional residual capacity, and total lung capacity of the mice in the CS+MST01 group significantly decreased and the lung function of forced expiratory volume 100 ms/forced vital capacity of the mice in the CS+MST01 group significantly increased after being induced with COPD by CS and simultaneously fed the P. goldsteinii of the present invention. The results demonstrate that the P. goldsteinii of the present invention can effectively improve the problem of the abnormal lung function of inspiratory capacity, lung chord compliance, functional residual capacity, total lung capacity, and forced expiratory volume 100 ms/forced vital capacity of individuals caused by COPD.

Example 4

Effect of Parabacteroides goldsteinii on Modulating the Lung Fibrosis-Related and the Mitochondrial Activity-Related Gene Expression Level in Lung Tissues of Chronic Obstruction Pulmonary Mice In order to investigate the effects of P. goldsteinii on modulating the lung fibrosis-related and the mitochondrial activity-related gene expression level in the COPD mice lung tissues, the lung tissues of each of these three mouse model groups were harvested from the mice. Quantitative PCRs (qPCR) with primers (see Table 1) specific to each of the target genes were performed. The 18S ribosomal primers were used as the internal control for qPCR assay. The total RNAs of lung tissue cells were extracted by using the Genezol TriRNA pure kit (Geneaid, New Taipei City, Taiwan). RNA was subjected to reverse transcription with Quant II fast reverse transcriptase kit (Tools, Taipei, Taiwan). The resulting cDNA (1 μn) was used as template and mixed with 1 μn of target gene primers, 5 μn of 2× qPCRBIO SyGreen Blue Mix Lo-ROX (PCR Biosystems, London, UK) and 3 μn double distilled water in each well. PCR conditions were performed as described below: initial step of pre-incubation at 95° C. for 3 min, followed by 50 PCR cycles of 95° C. for 10 secs, 60° C. for 20 secs, 72° C. for 5 secs and then one melting curve cycle.

TABLE 1

The sequence of the PCR primer

| Gene | Primer | Number | Length (ntds) |
|---|---|---|---|
| 18S ribosome | 18S ribosome-F | SEQ ID NO: 1 | 20 |
|  | 18S ribosome-R | SEQ ID NO: 2 | 20 |

TABLE 1-continued

The sequence of the PCR primer

| Gene | Primer | Number | Length (ntds) |
|---|---|---|---|
| RNR1 | RNR1-F | SEQ ID NO: 3 | 20 |
| | RNR1-R | SEQ ID NO: 4 | 20 |
| RNR2 | RNR2-F | SEQ ID NO: 5 | 22 |
| | RNR2-R | SEQ ID NO: 6 | 20 |
| TFAM | TFAM-F | SEQ ID NO: 9 | 22 |
| | TFAM-R | SEQ ID NO: 10 | 23 |
| NRF1 | NRF1-F | SEQ ID NO: 11 | 19 |
| | NRF1-R | SEQ ID NO: 12 | 21 |
| Cytb | Cytb-F | SEQ ID NO: 13 | 20 |
| | Cytb-R | SEQ ID NO: 14 | 20 |
| PGC-1α | PGC-1α-F | SEQ ID NO: 15 | 23 |
| | PGC-1α-R | SEQ ID NO: 16 | 22 |
| SIRT1 | SIRT1-F | SEQ ID NO: 17 | 20 |
| | SIRT1-R | SEQ ID NO: 18 | 20 |
| COL3A1 | COL3A1-F | SEQ ID NO: 19 | 20 |
| | COL3A1-R | SEQ ID NO: 20 | 20 |
| TNF-α | TNF-α-F | SEQ ID NO: 21 | 20 |
| | TNF-α-R | SEQ ID NO: 22 | 20 |
| IL-1β | IL-1β-F | SEQ ID NO: 23 | 20 |
| | IL-1β-R | SEQ ID NO: 24 | 20 |

Figure 10:
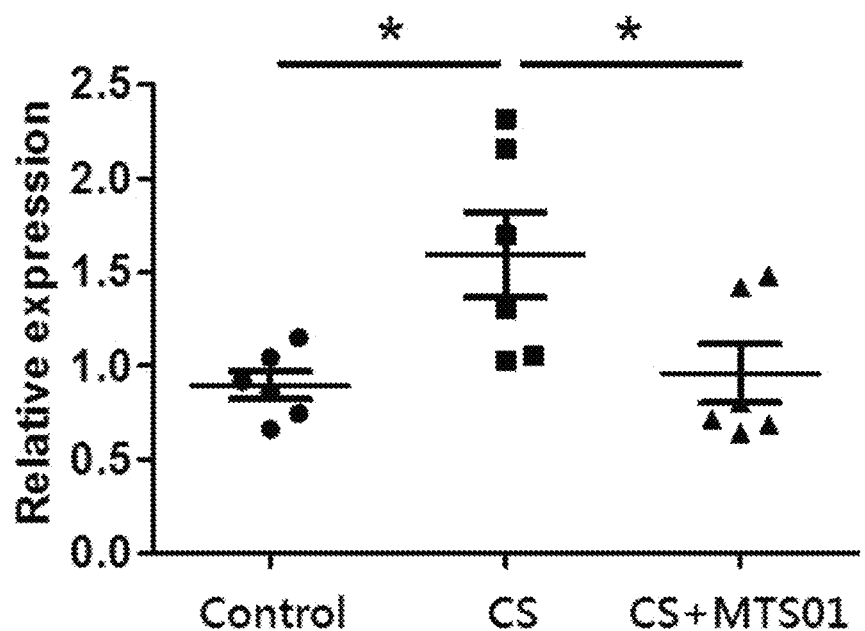
FIG. 10 shows that the *P. goldsteinii* reduces the gene expression level of IL-1β in the lung tissue in the COPD mice model. * $p<0.05$.
Figure 11:
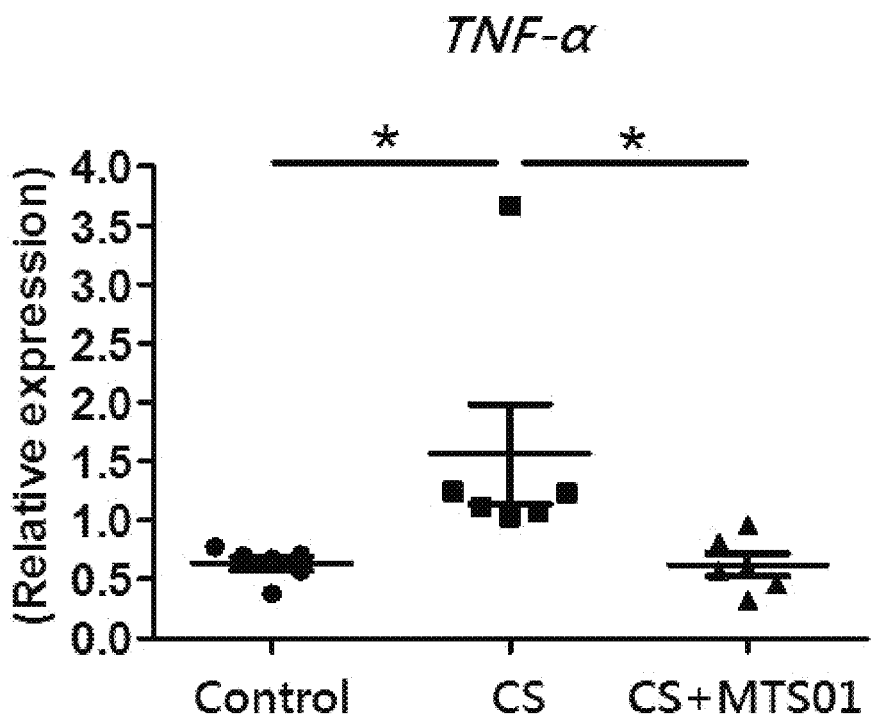
FIG. 11 shows that the *P. goldsteinii* reduces the gene expression level of TNF-α in the lung tissue in the COPD mice model. * $p<0.05$.
Figure 12:
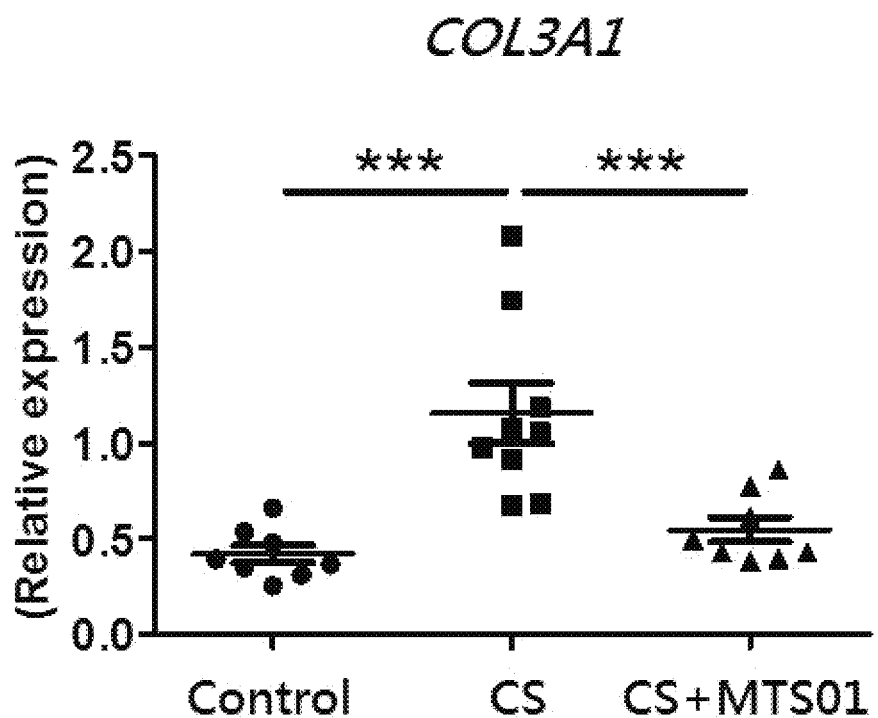
FIG. 12 shows that the *P. goldsteinii* reduces the gene expression level of COL3A1 in the lung tissue in the COPD mice model. *** $p<0.001$.
Figure 13:
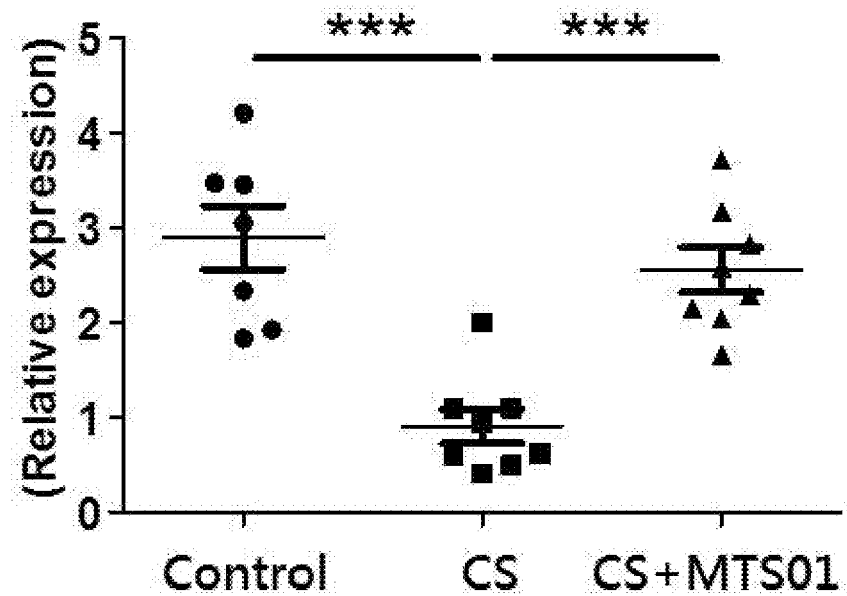
FIG. 13 shows that the *P. goldsteinii* induces the gene expression level of Cytb in the lung tissue in the COPD mice model. *** $p<0.001$.
Figure 14:
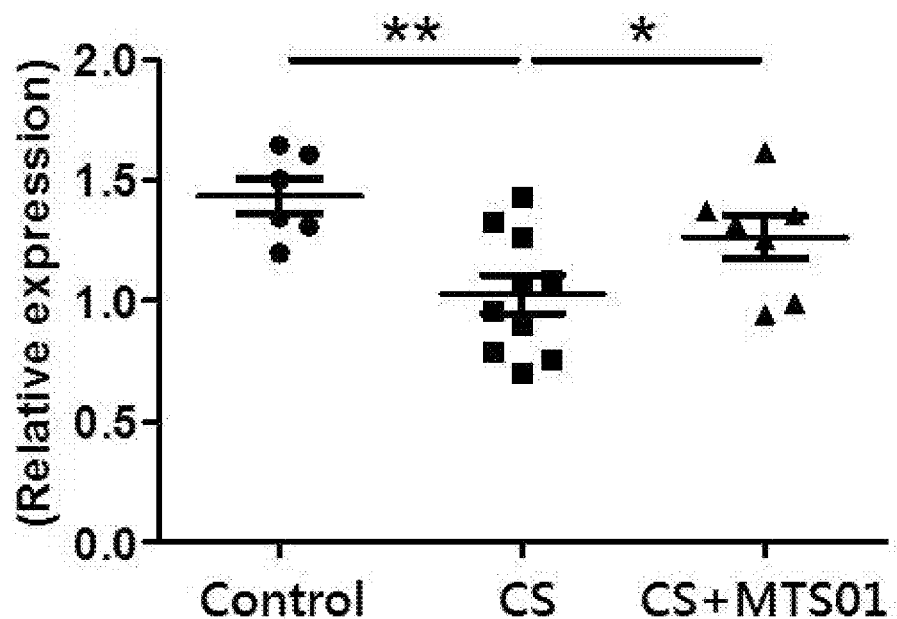
FIG. 14 shows that the *P. goldsteinii* induces the gene expression level of NRF-1 in the lung tissue in the COPD mice model. * $p<0.05$; ** $p<0.01$.
Figure 15:
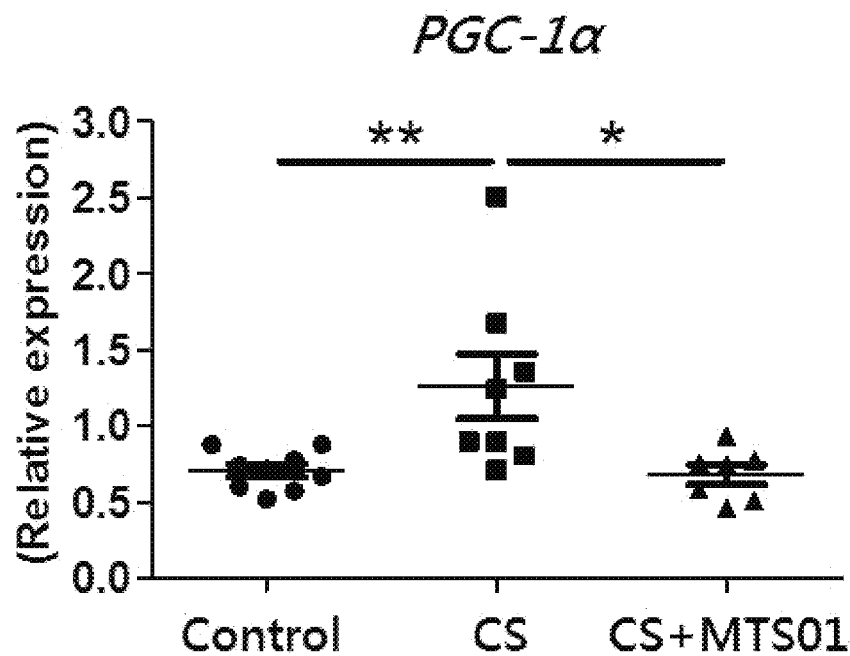
FIG. 15 shows that the *P. goldsteinii* reduces the gene expression level of PGC-1α in the lung tissue in the COPD mice model. * $p<0.05$; ** $p<0.01$.
Figure 16:
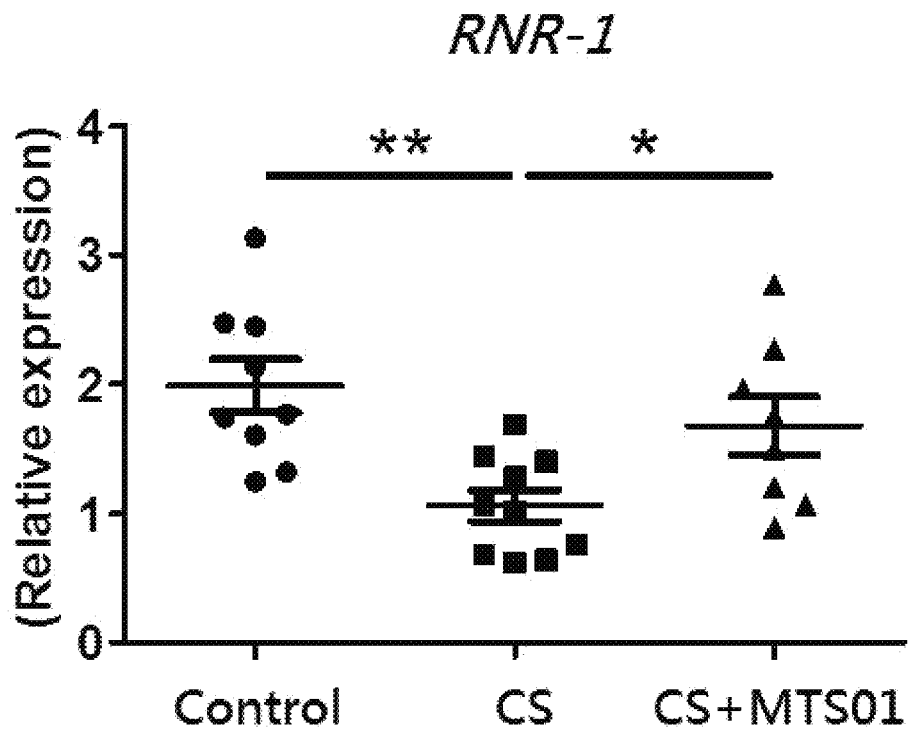
FIG. 16 shows that the *P. goldsteinii* induces the gene expression level of RNR-1 in the lung tissue in the COPD mice model. * $p<0.05$; ** $p<0.01$.
Figure 17:
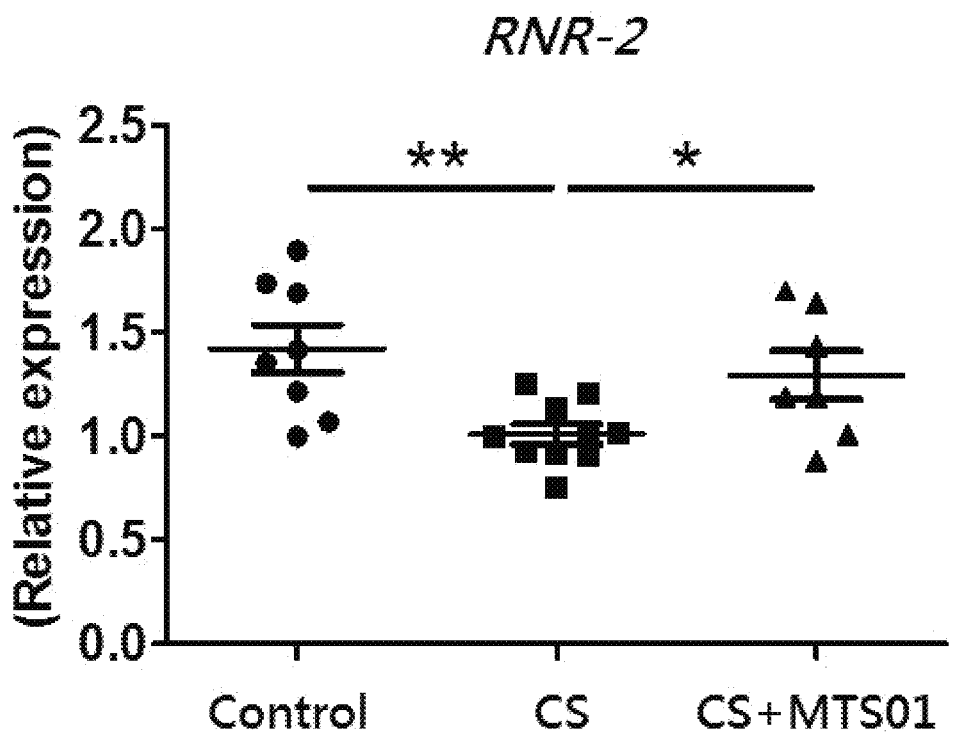
FIG. 17 shows that the *P. goldsteinii* induces the gene expression level of RNR-2 in the lung tissue in the COPD mice model. * $p<0.05$; ** $p<0.01$.
Figure 18:
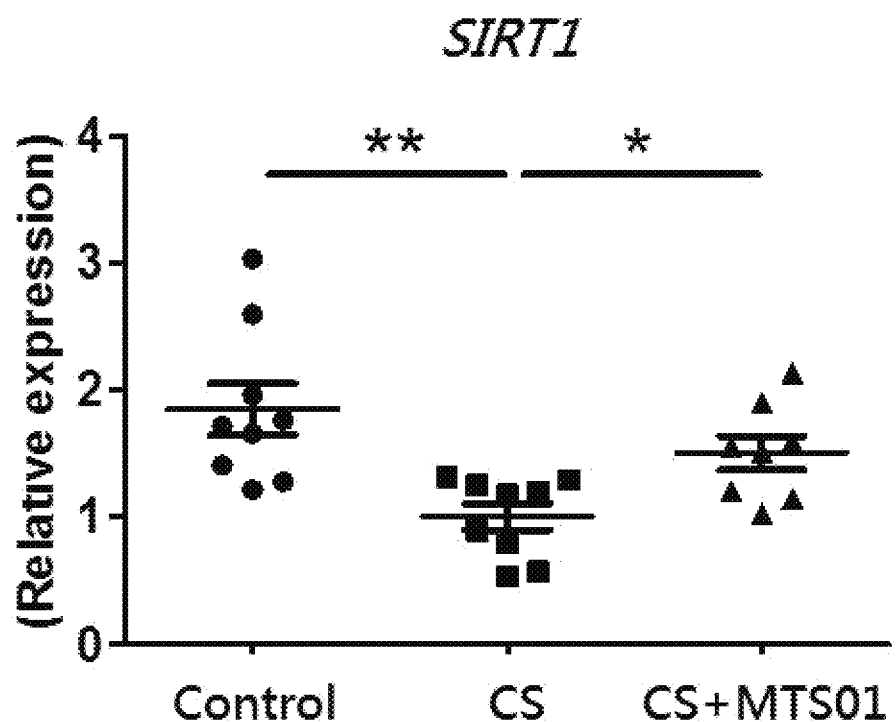
FIG. 18 shows that the *P. goldsteinii* induces the gene expression level of SIRT1 in the lung tissue in the COPD mice model. * $p<0.05$; ** $p<0.01$.
Figure 19:
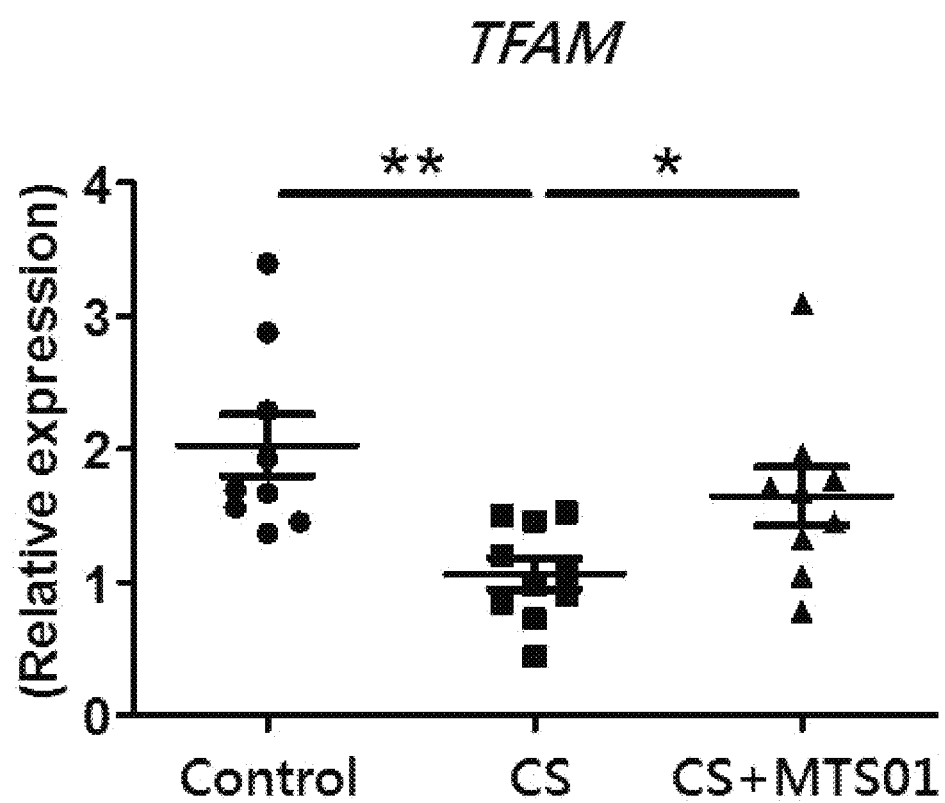
FIG. 19 shows that the *P. goldsteinii* induces the gene expression level of TFAM in the lung tissue in the COPD mice model. * $p<0.05$; ** $p<0.01$.

The results of the *P. goldsteinii* of the present invention for reducing the gene expression level of IL-1β in the lung tissue of CS-induced COPD mice are shown in FIG. 10; the results of the *P. goldsteinii* of the present invention for reducing the gene expression level of TNF-α in the lung tissue of CS-induced COPD mice are shown in FIG. 11; the results of the *P. goldsteinii* of the present invention for reducing the gene expression level of COL3A1 in the lung tissue of CS-induced COPD mice are shown in FIG. 12; the results of the *P. goldsteinii* of the present invention for inducing the gene expression level of Cytb in the lung tissue of CS-induced COPD mice are shown in FIG. 13; the results of the *P. goldsteinii* of the present invention for inducing the gene expression level of NRF-1 in the lung tissue of CS-induced COPD mice are shown in FIG. 14; the results of the *P. goldsteinii* of the present invention for reducing the gene expression level of PGC-1α in the lung tissue of CS-induced COPD mice are shown in FIG. 15; the results of the *P. goldsteinii* of the present invention for inducing the gene expression level of RNR-1 in the lung tissue of CS-induced COPD mice are shown in FIG. 16; the results of the *P. goldsteinii* of the present invention for inducing the gene expression level of RNR-2 in the lung tissue of CS-induced COPD mice are shown in FIG. 17; the results of the *P. goldsteinii* of the present invention for inducing the gene expression level of SIRT1 in the lung tissue of CS-induced COPD mice are shown in FIG. 18; the results of the *P. goldsteinii* of the present invention for inducing the gene expression level of TFAM in the lung tissue of CS-induced COPD mice are shown in FIG. 19.

IL-1β and TNF-α are important genes for promoting inflammation; COL3A1 is an important gene leading to lung fibrosis; Cytb is an important gene relating to the mitochondrial function; NRF-1, PGC-1α, RNR1, RNR2, SIRT1, and TFAM are important genes relating to the mitochondrial function and the activity of the anti-oxidative stress, wherein the studies has shown that the expression level of PGC-1α in mice with COPD would increase.

As showing in FIG. 10 to FIG. 19, compared with the control group, the gene expression level of IL-1β, TNF-α, COL3A1, and PGC-1α in lung tissues of the mice in the CS group significantly increased, and the gene expression level of Cytb, NRF-1, RNR1, RNR2, SIRT1, and TFAM significantly decreased. However, compared with the CS group, the gene expression level of IL-1β, TNF-α, COL3A1, and PGC-1α in lung tissues of the mice in the CS+MST01 group significantly decreased, and the gene expression level of Cytb, NRF-1, RNR1, RNR2, SIRT1, and TFAM significantly increased. The results demonstrate that the *P. goldsteinii* of the present invention can effectively decrease the gene expression level of IL-1β, TNF-α, COL3A1, and PGC-1α, which are related to lung fibrosis, and can effectively increase the gene expression level of Cytb, NRF-1, RNR1, RNR2, SIRT1, and TFAM, which are related to the mitochondrial function and the activity of the anti-oxidative stress.

The use of the *P. goldsteinii* of the present invention in the prevention or treatment of COPD can be, but is not limited to, oral administration to the subject in need thereof. The composition can be orally administered along with food; therefore, the preparation of the composition comprising the *P. goldsteinii* can further include a protein, a monosaccharide, a disaccharide, an oligosaccharide, an oligosaccharide, a polysaccharide, a carbohydrate, an amino acid, a lipid, a vitamin, or any combination well-known in the art.

Otherwise, the preparation of the composition comprising the *P. goldsteinii* can further include a pharmaceutically acceptable excipient, carrier, adjuvant, or food additive. The composition is in the form of a spray, a solution, a semi-solid state, a solid state, a gelatin capsule, a soft capsule, a tablet, ab oral strip, a chewing gum or a freeze-dried powder preparation. Simultaneously, the *P. goldsteinii* or the composition containing can further use in the preparation of a food, a health food, dietary supplement or vaccine composition.

In summary, the present invention provides the method of preventing or treating the COPD, comprising administering to the subject in need thereof the composition comprising the effective amount of the *P. goldsteinii*. The *P. goldsteinii* can improve the weight loss, the emphysema, the infiltration of inflammatory cells in lung tissues, the thickening of the tracheal wall, the lung fibrosis, and the abnormal lung function such as the abnormal inspiratory capacity, lung chord compliance (Cchord), functional residual capacity, total lung capacity, and forced expiratory volume 100 ms/forced vital capacity, which are all caused by the COPD. The *P. goldsteinii* can also reduce the gene expression level of IL-1β, TNF-α, COL3A1, or PGC-1α in lung tissues to reduce the inflammation, the lung fibrosis or oxidative stress in lung tissues; simultaneously, the *P. goldsteinii* can enhance the gene expression level of Cytb, NRF-1, RNR-1, RNR-2, SIRT1, or TFAM to enhance the mitochondrial activity of lung cells and to repair the mitochondrial dysfunction caused by COPD. Therefore, the *P. goldsteinii* of the present invention can be applied to the prevention or treatment of COPD and the preparation of the related compositions.

What is claimed is:

1. A method of treating a chronic obstructive pulmonary disease, comprising:
    administering to a subject in need thereof a composition comprising an effective amount of *Parabacteroides goldsteinii*; wherein, the *Parabacteroides goldsteinii* is *Parabacteroides goldsteinii* DSM32939.

2. The method according to claim 1, wherein the *Parabacteroides goldsteinii* is a live bacterium.

3. The method according to claim 1, wherein the effective amount of the *Parabacteroides goldsteinii* is at least $5\times10^9$ CFUs/kg of body weight per day.

4. The method according to claim 1, wherein the *Parabacteroides goldsteinii* ameliorates the weight loss, the infiltration of inflammatory cells in lung tissues, pro-inflammatory cytokine accumulation, airway smooth muscle hyperplasia, the emphysema, the lung fibrosis, or mitochondrial dysfunction, which are caused by the chronic obstructive pulmonary disease.

5. The method according to claim 1, wherein the composition further comprises other bacteria.

6. The method according to claim 1, wherein *Parabacteroides goldsteinii* reduces the inflammation in lung cells, the lung fibrosis or oxidative stress in lung cells.

7. The method according to claim 1, wherein *Parabacteroides goldsteinii* reduces the gene expression level of IL-Iβ, TNF-α, COL3A1, or PGC-1α.

8. The method according to claim 1, wherein *Parabacteroides goldsteinii* enhances the mitochondrial activity of lung cells.

9. The method according to claim 1, wherein *Parabacteroides goldsteinii* enhances the gene expression level of Cytb, NRF-1, RNR-1, RNR-2, SIRT1, or TFAM.

10. The method according to claim 1, wherein the composition further comprises a pharmaceutically acceptable excipient, carrier, adjuvant, or food additive.

11. The method according to claim 1, wherein the composition is in the form of a spray, a solution, a semi-solid state, a solid state, a gelatin capsule, a soft capsule, a tablet, an oral strip, a chewing gum or a freeze-dried powder preparation.

* * * * *